United States Patent [19]

Smith et al.

[11] 4,273,281
[45] Jun. 16, 1981

[54] INTERNAL SURGICAL STAPLER

[75] Inventors: Lawrence M. Smith; G. Marts Acker, both of Lake Oswego, Oreg.

[73] Assignees: Franklin G. Smith; Jerome F. Moshofsky, ; part interest to each

[21] Appl. No.: 59,941

[22] Filed: Jul. 23, 1979

[51] Int. Cl.³ .............................................. B25C 5/11
[52] U.S. Cl. ............................... 227/152; 227/DIG. 1
[58] Field of Search ................ 227/19, 134, 135, 152, 227/DIG. 1, DIG. 2, DIG. 3, DIG. 4

[56] References Cited

U.S. PATENT DOCUMENTS

| 3,017,637 | 1/1962 | Sampson | 227/DIG. 1 |
|---|---|---|---|
| 3,079,606 | 3/1963 | Bobrou et al. | 227/DIG. 1 |
| 3,482,428 | 12/1969 | Kapitanov et al. | 227/DIG. 1 |
| 3,494,533 | 2/1970 | Green et al. | 227/19 |
| 3,499,591 | 3/1970 | Green | 227/DIG. 1 |

Primary Examiner—Paul A. Bell

Attorney, Agent, or Firm—Klarquist, Sparkman, Campbell, Leigh, Whinston & Dellett

[57] ABSTRACT

The specification discloses an improved internal surgical stapler in which staples are pushed by a comb-like ram out of a magazine of a frame and are clinched by an anvil hinged to the frame and releasably latched to the frame by a latch. The latch includes a latch rod having a thumb grip and also provided with a leaf spring catch. The rod normally is in a retracted position in which its forward end is in the magazine. Then, when the user grips the thumb grip and the anvil and squeezes, the anvil is swung toward the magazine to clamp layers to be stapled and the rod is pushed out of the magazine and into a leaf spring latch in the anvil and latches. The rod is splined to the magazine until the end of this latching movement. To release the latch, the thumb grip is turned to turn the rod to move barbs on the rod out of latching holes in arms of the leaf spring catch.

4 Claims, 4 Drawing Figures

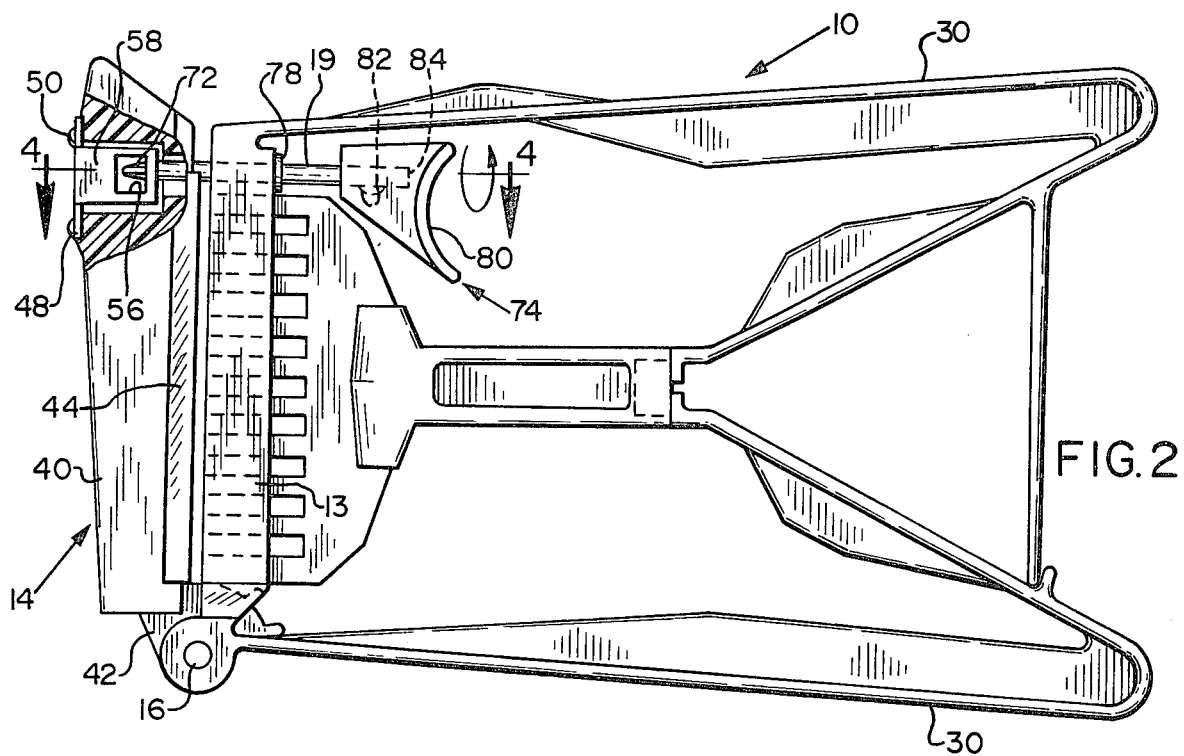
FIG. 2
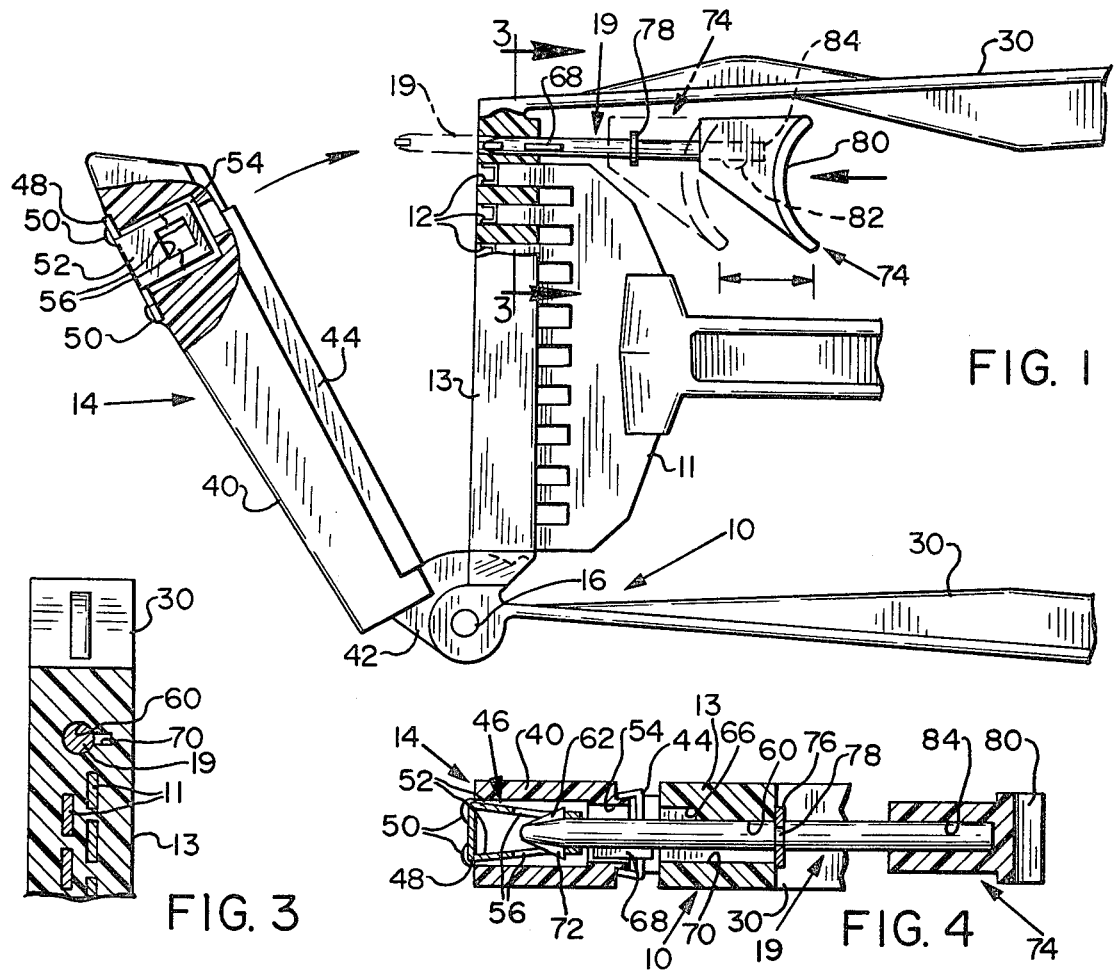
FIG. 1
FIG. 3
FIG. 4

INTERNAL SURGICAL STAPLER

DESCRIPTION

This invention relates to an improved internal surgical stapler, and has for an object thereof the provision of an improved internal surgical stapler.

Another object of the invention is to provide a stapler having a normally retracted latching rod.

Another object of the invention is to provide a stapler having a latching rod which is pushed out of a magazine into a catch in an anvil as the magazine and anvil are closed on layers to be stapled together, a thumb grip on the rod being used to push the rod and, after stapling, to turn the rod to a releasing position relative to the catch.

BRIEF DESCRIPTION OF THE DRAWINGS

In the drawings:

FIG. 1 is a fragmentary, side elevation view of an improved internal surgical stapler in an open condition and forming one embodiment of the invention;

FIG. 2 is a side elevation view of the stapler of FIG. 1 in a closed condition;

FIG. 3 is an enlarged vertical sectional view taken along line 3—3 of FIG. 1, and FIG. 4 is an enlarged, fragmentary horizontal sectional view taken along line 4—4 of FIG. 2.

Referring now in detail to the drawings, there is shown therein an improved internal surgical stapler forming a specific embodiment of the invention including a frame 10 adapted to drive comb-like rams 11 to move a multitude of suture staples 12 out of a magazine portion 13 thereof, through parts (not shown) to be sutured against an anvil 14 to clinch the staples. The anvil is hinged to the frame by a pin 16, and is manually movable between an open position as shown in FIG. 1 to a closed position as shown in FIG. 2 in which it is automatically latched by a latch 18 having a pointed piercing and latching rod 19 and a spring catch 20.

The frame 10 (FIGS. 1 and 2) is of a one-piece, molded, tough plastic construction, the material preferably being of an acetal such as "Delsin" or an acrylic, and includes a driving mechanism comprising a pair of handle or driving members 30 adapted to be gripped in one hand and squeezed toward each other to drive the rams 11 in their stapling movement. The general construction and operation of the driving mechanism is disclosed and claimed in copending application Ser. No. 059,667, filed July 23, 1979.

The anvil 14 includes a body 40 having a lug 42 hinging it to the frame 10 and also is provided with an anvil plate 44. The anvil construction and operation is generally like that disclosed and claimed in the above-mentioned copending application. A leaf spring catch 46 has a base 48 secured by rivets 50 to the body and has two spaced apart, spring arms 52 extending into a hole 54 through the free end portion of the body beyond the anvil plate 44. The arms have catch holes 56 therein.

Normally the latching rod 19 is held by friction in a retracted position in a bore 60 in magazine, a barb 62 on a pointed forward end 64 of the rod engaging an end of a short slot 66 in the magazine to act as a stop against upward movement of the rod as viewed in FIG. 4. The rod has a spline 68 which fits in a splining slot 70 in the magazine to hold the barb 62 and a second barb 72, which is one-hundred-eighty degrees from the barb 62, in alignment with the catch holes 56 until the last portion of forward movement of the rod relative to the magazine in latching. The spline 68 moves completely out of the magazine just before the barbs move under the catch holes to latch the anvil to the magazine, a thumb grip or pusher 74 fixed to and keyed to the rear end portion of the rod serving to push the rod forwardly until a split washer 76 trapped in a groove 78 in the rod engages the magazine. Then, with the anvil latched to the magazine in clamping position, the handle members 30 are squeezed together to effect the stapling and then are released to pull the ram plates 11 back to their normal positions. Then the thumb grip is manually turned ninety degrees to move the barbs 62 and 72 out of the catch holes 56, and, thus unlatched, the anvil is swung away from the frame to its open position. The pusher 74 has an arcuate thumb receiving notch 80, and the rod 19 has a keying tab 82 (FIGS. 1 and 2) swaged thereon and embedded in the pusher 74 when the rod is driven into a bore 84 (FIG. 4) in the pusher.

We claim:

1. In an improved internal surgical stapler,
holding means for holding a staple;
anvil means hinged to the holding means for clinching the staple and being movable between an open position and a clamping position clamping layers to be stapled together;
a latching pin;
latching means carried by the anvil means;
means mounting the latching pin on the holding means for forward movement from a retracted position to a latching position engaging the latching means when the anvil means is in its clamping position; and
manually operable release means for effecting unlatching of the pin and the latching means,
the release means including means for turning the pin relative to the latching means, wherein the pin and the latching means are disengageable.

2. The stapler of claim 1 including a thumb grip on the pin for pushing the pin from its retracted position to its latching position and keyed to the pin for turning the pin relative to the latching means to effect unlatching.

3. The stapler of claim 2 wherein the latching pin includes a latching barb on one side thereof,
the latching means including a catch adapted to be engaged by the barb only when said one side is adjacent the catch.

4. The stapler of claim 3 wherein the holding means has a bore therein and a splining groove,
the pin having a spline positioned in the groove except when the pin is extended to its latching position.

* * * * *